US012779201B2

(12) United States Patent
Aboulhosn et al.

(10) Patent No.: US 12,779,201 B2
(45) **Date of Patent: *Nov. 3, 2026**

(54) CANNULA FOR INTRAVASCULAR BLOOD PUMP

(71) Applicant: Abiomed Europe GmbH, Aachen (DE)

(72) Inventors: Walid Aboulhosn, Aachen (DE); Thorsten Siess, Aachen (DE); Frank Kirchhoff, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 98 days.

This patent is subject to a terminal disclaimer.

(21) Appl. No.: 18/227,342

(22) Filed: Jul. 28, 2023

(65) Prior Publication Data

US 2024/0058593 A1 Feb. 22, 2024

Related U.S. Application Data

(63) Continuation of application No. 16/625,491, filed as application No. PCT/EP2018/066590 on Jun. 21, 2018, now Pat. No. 11,752,322.

(30) Foreign Application Priority Data

Jun. 21, 2017 (EP) .................................... 17177180
Aug. 2, 2017 (EP) .................................... 17184552

(51) Int. Cl.
*A61M 60/178* (2021.01)
*A61M 25/00* (2006.01)
(Continued)

(52) U.S. Cl.
CPC ...... *A61M 60/178* (2021.01); *A61M 25/0012* (2013.01); *A61M 60/13* (2021.01);
(Continued)

(58) Field of Classification Search
CPC .... A61M 60/857; A61M 60/855; B29D 23/00
See application file for complete search history.

(56) References Cited

U.S. PATENT DOCUMENTS 4,250,072 A 2/1981 Flynn
4,675,361 A 6/1987 Ward
(Continued)

FOREIGN PATENT DOCUMENTS

CN 102341141 A 2/2012
EP 2841124 A1 3/2015
(Continued)

OTHER PUBLICATIONS

Hearing Notice for Indian Application No. 20193704645, dated Mar. 23, 2024 (2 pp.).
(Continued)

*Primary Examiner* — Scott Luan
(74) *Attorney, Agent, or Firm* — Botos Churchill IP Law LLP

(57) ABSTRACT

A method of manufacturing a cannula (4) for an intravascular blood pump comprises the steps of forming a first axial section (13) and a second axial section (15) of an elongate tubular body of the cannula (4) by dispensing a first liquid material and a second liquid material, respectively, onto a mandrel (7) by means of at least one dispenser (8). The mandrel (7) is rotated and the dispenser (8) moves relative to the mandrel (7) in an axial direction during dispensing of the liquid materials. The first and second axial sections (13, 15) are formed so as to have different bending stiffnesses. The first and second liquid materials are dispensed onto the mandrel (7) such that the first and second liquid materials blend into each other to form a smooth transition area (14).

15 Claims, 7 Drawing Sheets

(51) Int. Cl.

| | |
|---|---|
| ***A61M 60/13*** | (2021.01) |
| ***A61M 60/174*** | (2021.01) |
| ***A61M 60/216*** | (2021.01) |
| ***A61M 60/857*** | (2021.01) |
| ***B29D 23/00*** | (2006.01) |

(52) U.S. Cl.

CPC ........ *A61M 60/174* (2021.01); *A61M 60/216* (2021.01); *A61M 60/857* (2021.01); *B29D 23/00* (2013.01)

(56) References Cited

U.S. PATENT DOCUMENTS

| | | | | |
|---|---|---|---|---|
| 5,403,292 | A | 4/1995 | Ju | |
| 5,533,985 | A * | 7/1996 | Wang | B29C 48/21 604/525 |
| 5,827,242 | A | 10/1998 | Follmer et al. | |
| 5,951,929 | A | 9/1999 | Wilson | |
| 6,007,478 | A * | 12/1999 | Siess | A61M 25/0053 600/585 |
| 6,790,171 | B1 | 9/2004 | Gruendeman et al. | |
| 8,888,728 | B2 | 11/2014 | Aboul-Hosn et al. | |
| 11,752,322 | B2 * | 9/2023 | Aboulhosn | B29D 23/00 600/16 |
| 2003/0230823 | A1 * | 12/2003 | Bartholomew | B29C 41/36 264/156 |
| 2004/0065979 | A1 | 4/2004 | Wang | |
| 2005/0182475 | A1 | 8/2005 | Jen et al. | |
| 2012/0172655 | A1 | 7/2012 | Campbell et al. | |
| 2014/0012065 | A1 | 1/2014 | Fitzgerald et al. | |
| 2015/0306282 | A1 | 10/2015 | Scanlon et al. | |
| 2015/0328382 | A1 | 11/2015 | Corbett et al. | |
| 2016/0279310 | A1 | 9/2016 | Scheckel et al. | |

FOREIGN PATENT DOCUMENTS

| | | | |
|---|---|---|---|
| JP | H11239617 | A | 9/1999 |
| JP | 2007503916 | A | 3/2007 |
| WO | 2013160443 | A1 | 10/2013 |

OTHER PUBLICATIONS

International Search Report and Written Opinion for International Application No. PCT/EP2018/066590 dated Aug. 17, 2018, 10 pp.

Office Action from Chinese Application No. 201880041629.7 dated Oct. 8, 2022 (16 pages).

Office Action from Chinese Patent Application No. 201880041629.7 dated Jan. 18, 2022, 17 pp.

Office Action from European Patent Application No. 18 732 783.8 dated May 4, 2023. (6 pp.).

Office Action from Indian Patent Application No. 201937047645 dated Feb. 25, 2022, (6 pp.).

Office Action from Israeli Patent Application No. 270715 dated May 30, 2023 (5 pp.).

Office Action from Japanese Application No. 2019-571314 dated Sep. 6, 2022 (14 pages).

Office Action from Japanese Patent Application No. 2019-571314 dated Apr. 11, 2023 (10 pp.).

Office Action from Korean Patent Application No. 10-2020-7000939 dated Mar. 22, 2023 (18 pages).

Written opinion for SG Application No. 11201910969V dated Aug. 17, 2022 with English Translation (5 pages).

Office Action issued in Israeli Patent Application No. 270715 on Aug. 22, 2024 (4 pp.).

Office Action from Japanese Patent Application No. 2024-125725 dated Nov. 4, 2025 (4 pp.).

* cited by examiner

CANNULA FOR INTRAVASCULAR BLOOD PUMP

CROSS-REFERENCE TO RELATED APPLICATIONS

This application is a continuation of U.S. application Ser. No. 16/625,491, filed Dec. 20, 2019, now U.S. Pat. No. 11,752,322, which application is a United States National Stage filing under 35 U.S. C. § 371 of International Application No. PCT/EP2018/066590, filed Jun. 21, 2018, which claims priority to European Patent Application No. 17177180.1, filed Jun. 21, 2017 and European Patent Application No. 17184552.2, filed Aug. 2, 2017. The contents of each of the foregoing applications are hereby incorporated by reference in their entirety. International Application No. PCT/EP2018/066590 was published under PCT Article 21 (2) in English.

BACKGROUND OF THE INVENTION

This invention relates to a method of manufacturing a cannula for an intravascular blood pump for percutaneous insertion into a patient's blood vessel, as well as a cannula obtainable by said method.

Intravascular blood pumps are used to support the function of a patient's heart, either as a left ventricular assist device (LVAD) or right ventricular assist device (RVAD). An intravascular blood pump for percutaneous insertion typically comprises a catheter and a pumping device and is inserted into the patient's heart, e.g. through the aorta into the left ventricle. The pumping device comprises a blood flow inlet and a blood flow outlet and a cannula through which the blood flow is created e.g. by a rotor of the pumping device. For example, the cannula may extend through the aortic valve with the blood flow inlet disposed at a distal end of the cannula in the left ventricle and the blood flow outlet disposed at a proximal end of the cannula in the aorta.

The cannula may be relatively soft and flexible, e.g. made of silicone, soft polyurethane or polyester (Dacron®) to reduce the risk of causing damage to a cardiac valve. However, if a very soft cannula is connected to the housing of the pumping device, which is e.g. made of metal, the cannula's material at the interface between the housing of the pumping device and the cannula may crack because the interface is subject to high loads. There is also a high risk that thrombi form in the cracks of the material, which may cause harm to the patient if they separate from the blood pump and are transported through the vascular system. A stiffer cannula may be made e.g. from hard polyurethane. However, if the cannula is too stiff, side movements of the cannula in the cardiac valve may cause harm to the valve's leafs. It is also known to increase the strength of a soft cannula by incorporating a helical wire, e.g. a Nitinol wire. However, this may lead to a scissor-like effect at the interface between the housing of the pumping device and the cannula and may, thus, damage the material of the cannula. Thus, in view of the aforementioned, the cannula should be soft enough to avoid damage to the cardiac valve but should provide sufficient stiffness to avoid damage of the material.

BRIEF SUMMARY OF THE INVENTION

It is an object of the present invention to provide an improved method of manufacturing a cannula for an intravascular blood pump that has a stiffness to withstand loads during operation of the blood pump while not causing harm to the patient's body.

This object is achieved according to the present invention by a method of manufacturing a cannula for an intravascular blood pump and a cannula obtained by such method having the features of the independent claims. Preferred embodiments and further developments of the invention are specified in the claims dependent thereon. Throughout this disclosure, the term "distal" refers to directions away from a user and towards the heart, whereas the term "proximal" refers to directions towards a user.

Broadly speaking, according to the invention, a cannula for an intravascular blood pump is manufactured by dispensing liquid material onto an elongate element, such as a mandrel. Preferably, the liquid material is applied in layers which dry or cure to form different axial sections of an elongate tubular body of the cannula. The mandrel is removed after the body is completed. This method allows adjusting the characteristics of the cannula, such as bending stiffness, along the length of the cannula. Rather than attaching different axial sections to one another, e.g. by welding, bonding, adhesive or the like, the axial sections of the cannula of the present invention are produced by dispensing liquid material onto a mandrel such that no distinct borders can be determined between the axial sections but blend smoothly into one another. Thus, material borders can be avoided at which high stresses could occur during operation of the blood pump.

More specifically, according to one embodiment, the method comprises the step of forming a first axial section of the cannula's body by dispensing a first liquid material onto a mandrel by means of at least one dispenser, while the mandrel and the dispenser move relative to each other in an axial direction and a circumferential direction of the mandrel. The method further comprises the step of forming a second axial section by dispensing a second liquid material onto the mandrel by means of the at least one dispenser, while the mandrel and the dispenser move relative to each other in an axial direction and a circumferential direction of the mandrel.

The first and second liquid materials are dispensed onto the mandrel such that the first and second liquid materials blend into each other to form a transition area. For instance, the transition area may extend over an axial length of at least 10 μm to provide a smooth transition between the first and second axial sections. The first and second axial sections are formed so as to have different bending stiffnesses. The first and second materials may be dispensed by a single dispenser or different dispensers. In case only one dispenser is used, the first and second materials may be dispensed by a single nozzle or different nozzles of the dispenser.

As mentioned above it will be appreciated that the method preferably further comprises the step of curing or drying the dispensed layers of liquid material to form the final product. In particular, the materials may be at least partially dried or cured before the next layer of a liquid material is dispensed. A liquid material may be a material comprising a solvent as described hereinafter in more detail, a molten material, an extruded material or the like having a viscosity which is suitable to allow dispensing the material onto the rotating mandrel. In particular, the one or more materials of the cannula may be a polymer material or polymer materials.

In other words, a cannula that can be obtained by the aforementioned method has an elongate tubular body with a blood flow inlet and a blood flow outlet, wherein the body comprises a first axial section comprising a first material and a second axial section comprising a second material, wherein the first and second axial sections have different bending stiffnesses, and wherein the first and second materials blend into each other in a transition area. The cannula may have more than two axial sections with different bending stiffnesses. For example, one or more flexing portions having a low bending stiffness can be created that connect stiffer axial sections with a greater bending stiffness. The lengths of the axial sections can be chosen as desired, e.g. depending on the application. For example, the flexing portions can be shorter or longer than the stiffer portions.

In one embodiment, the first and second liquid materials are dispensed onto the mandrel to form a first wall thickness of the first axial section and a second wall thickness of the second axial section, respectively, wherein the first wall thickness is different from the second wall thickness. Alternatively or in addition, the first and second liquid materials may be different. The different bending stiffnesses may result from at least one of the differing wall thicknesses and the differing materials. Throughout this disclosure, the term "wall thickness" and respective values given for the wall thickness refer to the final state of the cannula, i.e. in particular after curing or drying of the materials, unless otherwise indicated.

In case the first and second materials are different, they may axially overlap in the transition area. Suitable materials are soft polyurethane, hard polyurethane, polyethylene, silicone or the like. It will be appreciated that the first and second materials may be identical. Instead of overlapping, the materials may blend into each other, independently of whether they are identical or different. The wall thicknesses may be influenced by a variety of parameters, such as material, dispensed amount of material, dispensing rate, speed of movement of one or both of the mandrel and the dispenser, and proportion of solvent in the materials etc. as will be described in more detail below. Thus, the characteristics, in particular the bending stiffnesses, of the first and second axial section can be adjusted as desired.

The first axial section may be a proximalmost section or a distalmost section of the cannula's body and may have a greater bending stiffness than the second axial section or the rest of the cannula's body. In particular, the section connecting to a housing of a pumping device may have a greater bending stiffness than the rest of the cannula's body. This provides sufficient strength at the interface between the cannula and the housing of the pumping device, and at the same time provides soft characteristics of the cannula to avoid damages to surrounding tissue, such as a cardiac valve.

As mentioned above, the mandrel and the dispenser move relative to each other in an axial direction and a circumferential direction of the mandrel during dispensing of the liquid materials onto the mandrel. This may be achieved by rotating the mandrel about its longitudinal axis, e.g. on a lathe, and moving the dispenser in an axial direction along the mandrel while dispensing the first and second liquid materials. The mandrel is preferably rotated at a speed of about 10 to 15 rpm (revolutions per minute), more preferably at about 12 rpm. It will be appreciated that the dispenser may be alternatively fixed in an axial direction and the rotating mandrel may be moved in an axial direction. It may also be possible to move the dispenser in a circumferential direction about the mandrel, e.g. if the liquid materials are sprayed onto the mandrel. A person skilled in the art will understand that any combination of axial and circumferential or rotational movement of the mandrel and the dispenser, respectively, may be suitable to achieve the desired relative movement between the mandrel and the dispenser. Preferably, the mandrel has a circular cross-section, but other cross-sectional shapes are possible. The mandrel may have a length of about 1 cm to 40 cm, which will result in a cannula having a length of about 1 cm to 40 cm. The mandrel may have a diameter of about 1 mm to 10 mm, which will result in a cannula having an inner diameter of about 1 mm to 10 mm.

The method may further comprise the step of forming a base layer that extends along the entire length of the cannula's body by dispensing a third liquid material onto the mandrel. The base layer is preferably formed by dispensing a substantially uniform amount of the third liquid material with respect to the length of the mandrel, wherein the base layer preferably has a thickness of about 50 μm to 100 μm. The third material may be different from the first and second materials or may be identical to at least one of the first and second materials. The base layer may be provided to create a uniform support for the tubular body of the cannula, while the characteristics of the first and second axial sections are adjusted by subsequent layers of the first and second materials that are applied onto the base layer. Other specific layers or axial sections with specific properties can be included in the cannula. For example, an area for enhanced metal adhesion can be created by providing a primer layer. One or more layers may be provided with a medical agent, such as heparin, to avoid clot formation on the surface of the cannula's body.

The method may further comprise the step of forming a stiffening structure by dispensing a fourth liquid material on the mandrel, preferably a polymer material, wherein the first and second liquid materials are preferably dispensed both before and after dispensing the fourth material so as to embed the stiffening structure in the cannula's body. The stiffening structure may be formed along a helical path or any other suitable structure, such as longitudinal or circumferential struts or a grid structure. The fourth material has preferably a higher Young's modulus (elastic modulus) than the first and second materials in order to provide sufficient strength to form a stiffening structure. For example, the fourth material of the stiffening structure may be hard polyurethane, while the first and second materials may be soft polyurethane, polyethylene or silicone. That means the elongate tubular body of the cannula may comprise an embedded stiffening structure made of a plastic material rather than embedding a stiffening structure made of a metal. Alternatively or in addition, the cannula's body may comprise a stiffening structure that comprises a thread or wire, which may be made of metal, preferably a shape memory material, such as Nitinol, or may be made of a polymer. The wire may extend in a helical shape about the cannula. If it is made of a metal it may be pre-wound before it is added to the cannula. Alternatively, the thread or wire, e.g. if made of a polymer, may be wound around the mandrel along a helical path or other suitable pattern, e.g. two opposite helical paths crossing each other, or other braid pattern. For instance, the helical wire may be embedded into the cannula's body between layers of the first and second materials.

Advantageously, at least one of the first and second liquid materials comprises a solvent that evaporates after dispensing the first and second liquid materials, respectively, wherein the proportion of the solvent is at least 70%, preferably at least 80%, more preferably at least 90%. The proportion of the solvent is preferably measured in percent by volume (vol %), but may alternatively be measured in percent by weight if appropriate. The solvent preferably evaporates but may alternatively or in addition be absorbed by the mandrel, which may be provided with a porous structure for this purpose. The first and second materials may comprise the same proportion of solvent or a different proportion of solvent that blend into each in the transition area. If the proportion of solvent is different, this will result in different wall thicknesses or the respective sections after the solvent has evaporated, i.e. after drying.

The provision of a solvent in the liquid materials facilitates manufacture of very thin layers because the major part of the applied material evaporates after dispensing on the mandrel. That means that the layers of liquid material "physically dry" on the mandrel before another layer of liquid material is dispensed. However, the layers should not completely dry and cure before a subsequent layer is dispensed in order to ensure that the subsequent layers sufficiently blend to form an integral elongate tubular body. Preferably, at least one of the first and second axial sections is formed by dispensing at least 5, preferably at least 10, up to 20 layers of the first and second liquid materials, respectively. This may result in a cannula having an elongate tubular body with a wall thickness in the range from about 50 μm to about 500 μm, after drying and curing of the materials. Generally, any number of layers, different materials, axial sections etc. may be produced as desired. Additional layers may be created by at least partially dipping the cannula manufactured by the described dispensing method into a liquid material.

In one embodiment, the mandrel may have a circumferential shoulder interconnecting two axially adjacent parts of the mandrel with different diameters, wherein the two axially adjacent parts of the mandrel are preferably separated from each other to remove the cannula from the mandrel. Thus, the elongate tubular body of the cannula may have a circumferential shoulder interconnecting two axially adjacent sections of the body with different diameters.

The method may further comprise the step of forming at least one marking arranged on the cannula's body, wherein the at least one marking may be visually perceptible, e.g. by exhibiting a different color than the cannula's body, or may be radiopaque so as to be visible under x-ray. Preferably, the at least one marking is formed by dispensing a liquid material by means of the dispenser. The at least one marking may extend on or may be embedded in the elongate tubular body. For example, the marking may be a colored band that extends about the cannula's body.

The method may further comprise the step of forming a lumen extending in the wall of the cannula's body by embedding an elongate element in the wall of the cannula's body. The elongate element may be a hollow tubular element that remains in the cannula's body to form the lumen. Alternatively, the elongate element may be a solid filament that is removed from the cannula's body to form the lumen.

The method may further comprise the step of forming at least one aperture in the cannula's body by dispensing a liquid material onto the mandrel, optionally without rotating the mandrel or with rotating the mandrel very slowly, while dispensing said liquid material. In particular, a cage structure at one end of the cannula can be formed by dispensing material onto the mandrel, which is similar to a 3D printing process. A viscosity of the material is chosen so as to prevent dropping of the material but allowing merging with other printed areas or earlier or later dispensed layers of the cannula's body. Thus, a structure that is printed in this manner will attach to the body of the cannula and form an integral part of the cannula.

The method may further comprise the step of attaching the cannula to a housing of a pumping device of an intravascular blood pump, i.e. the invention also relates to an intravascular blood pump for percutaneous insertion into a patient's blood vessel, comprising a cannula obtained by the above-described method.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
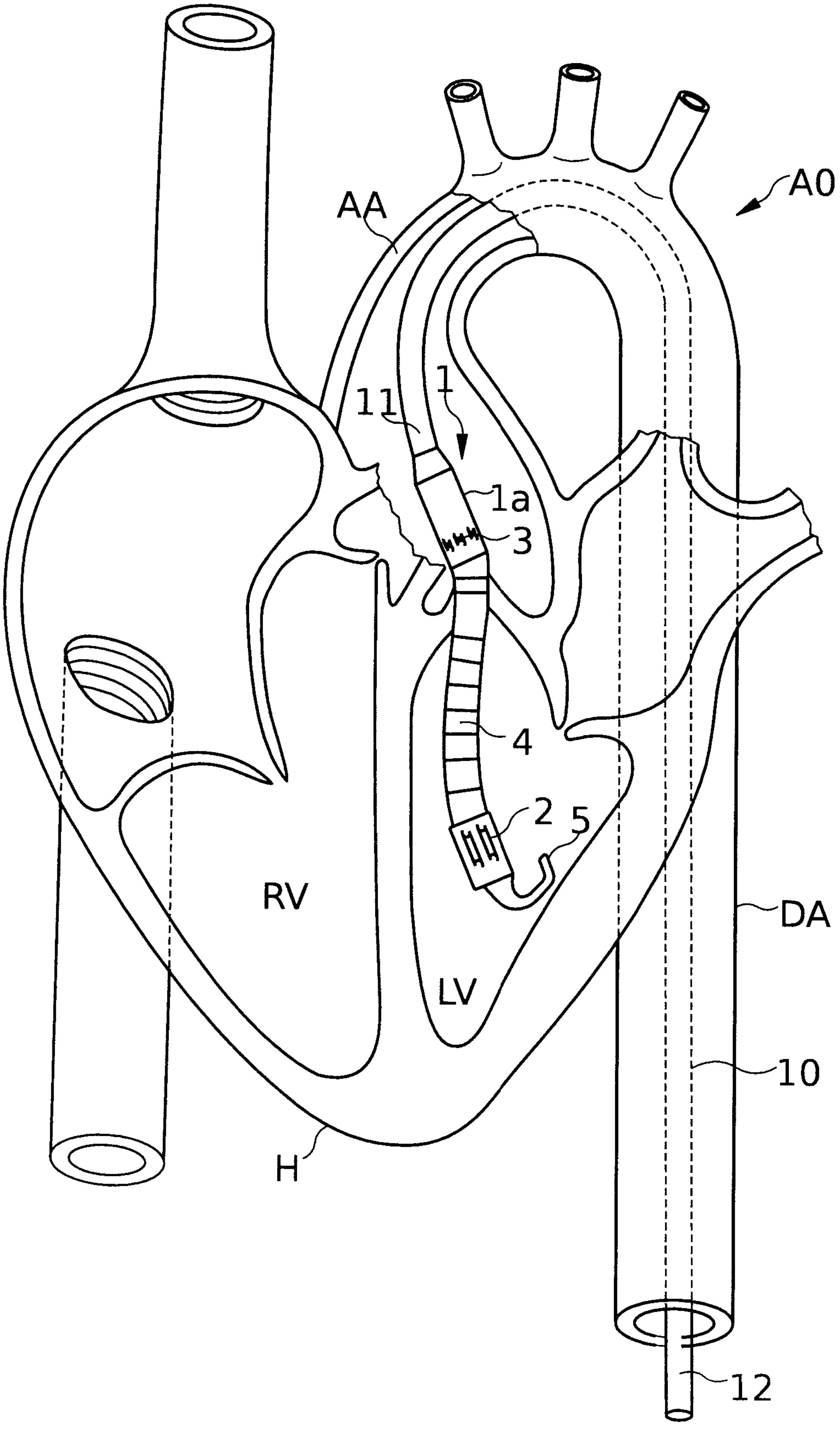
FIG. 1 shows a patient's heart with an intravascular blood pump inserted through the aorta into the left ventricle.

In FIG. 1 is illustrated a blood pump inserted into a patient's heart H. More specifically, the blood pump comprises a pumping device 1 attached to a catheter 10 by means of which the pumping device 1 is inserted into the left ventricle LV of the patient's heart H via the aorta AO, including the descending aorta DA and the aortic arch AA. The catheter 10 has a distal end 10*a* and a proximal end 10*b*. The pumping device 1 has a blood flow outlet 3 that is disposed outside the patient's heart H in the aorta AO, while a blood flow inlet 2 is in flow communication with a cannula 4 placed inside the left ventricle LV. An impeller (not shown) is provided in a housing 1*a* of the pumping device 1 to cause the blood flow from the blood flow inlet 2 to the blood flow outlet 3. At the distal end of the blood pump, a soft tip 5, such as a pigtail or J-tip, is arranged to facilitate insertion of the blood pump into the patient's heart H without causing any harm to the surrounding tissue. Also, the soft tip 5 helps to keep soft tissue away from the cannula 4.

Figure 2:
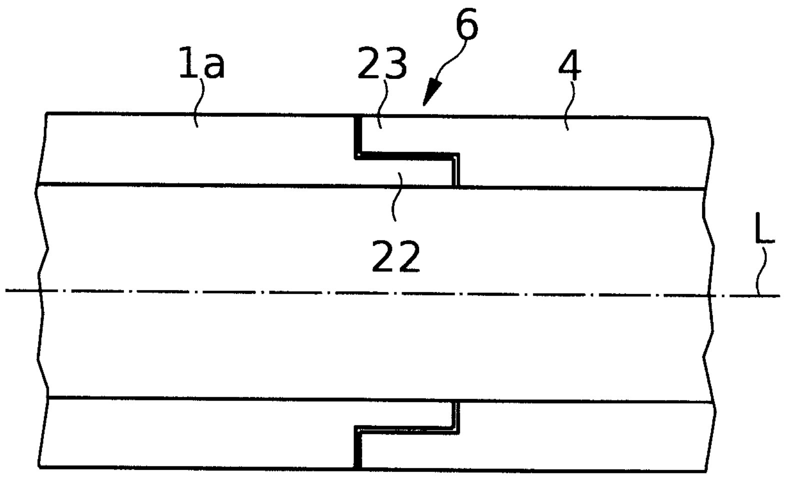
FIG. 2 shows an enlarged view of the interface between the cannula and the housing of the pumping device of an intravascular blood pump.

FIG. 2 shows an enlarged schematic cross-sectional view of the interface 6 between the housing 1*a* of the pumping device 1 and the cannula 4. The housing 1*a* and the cannula 4 are stepped at their respective ends 22, 23 which are to be attached to one another. While the housing 1*a* of the pumping device 1 may be made of metal, the cannula 4 may be made of a plastic material, such as silicone, polyethylene or polyurethane. At the interface 6 between the relatively hard material of the housing 1*a* of the pumping device 1 and the relatively soft material of the cannula 4 the loads during operation of the blood pump may cause cracks in the material of the cannula 4. Therefore, it is desirable to increase the bending stiffness of the cannula 4 in the region of the interface 6. However, the rest of the cannula 4 should be softer to avoid damages to the surrounding tissue, such as the leafs of a cardiac valve.

A method of manufacturing a cannula 4 that can exhibit different characteristics along its length, in particular different bending stiffnesses, is shown schematically in FIGS. 3*a* to 3*d*. The core idea of the method is that the cannula is produced by dispensing liquid material onto an elongate element, such as a mandrel, rather than attaching different sections to one another. The following steps are shown schematically and not true to scale for illustrative purposes. In particular, for the sake of simplicity, the steps are shown only for a single layer in each axial section. It will be appreciated, however, that more than one, up to 20 layers or more, may be applied in each axial section.

Figure 3A:
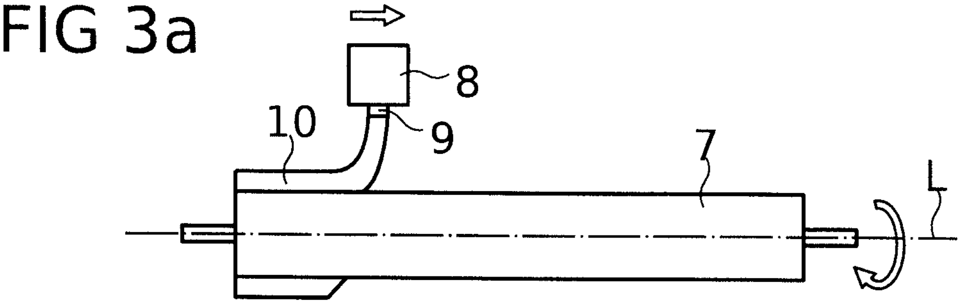
FIGS. 3*a* to 3*d* show steps of a method of manufacturing the cannula.

In a first step, shown in FIG. 3*a*, a base layer 10 is applied onto a mandrel 7. In order to create the base layer 10, a liquid material is applied onto the mandrel 7 by means of a dispenser 8 having at least one nozzle 9 to dispense the liquid material. During dispensing the liquid material, the mandrel 7 is rotated about its longitudinal axis L, which is coincident with the longitudinal axis L of the cannula 4. The mandrel 7 may be rotated by means of a suitable apparatus, such as a lathe (not shown). The speed of rotation may be about 12 rpm. The dispenser 8 is moved in an axial direction along the length of the mandrel 7. The axial speed of the dispenser 8 and the rotational speed of the mandrel 7 are chosen such that a continuous layer of liquid material can be applied along the length and about the circumference of the mandrel 7. The final base layer 10, i.e. after drying and curing, may have a thickness of about 50 μm to 100 μm.

Figure 3B:
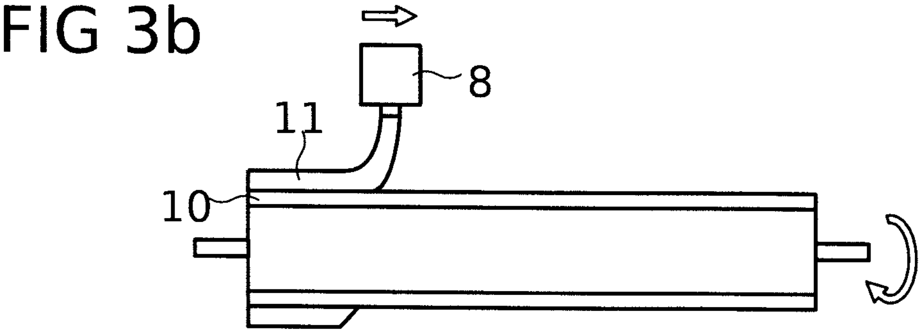

After the base layer 10 is fully applied onto the mandrel 7 and at least dried to a desired degree, as will be explained in more detail below with respect to FIG. 5, a layer 11 of a liquid material is applied in the same manner as the base layer 10, i.e. by moving the dispenser 8 along the longitudinal direction of the mandrel 7, while the mandrel 7 is rotated, as shown in FIG. 3*b*. The liquid material of the layer 11 may be the same material as the material of the base layer 10 or a different material. The same dispenser 8 may be used. In particular, if the material is different, it may be dispensed by another nozzle of the dispenser 8 or possibly another dispenser. The layer 11 is part of a first axial section 13 of the cannula 4 (see FIG. 3*d*) and is applied only along a part of the length of the mandrel 7.

Figure 3C:
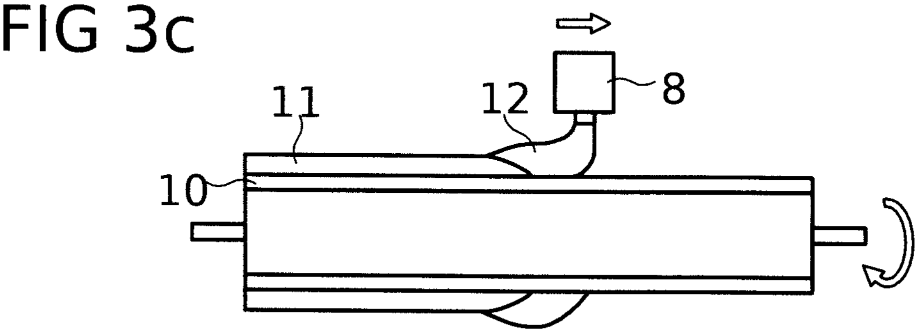

As shown in FIG. 3*c*, a layer 12 of another liquid material is applied axially adjacent the layer 11 onto the mandrel 7 in the same manner as described above, i.e. by moving the dispenser 8 along the longitudinal direction of the mandrel 7, while the mandrel 7 is rotated. The material of the layer 12 may be different from the material of the layer 11. As indicated in FIG. 3*c*, the layer 12 is thicker than the layer 11. The layer 12 is part of a second axial section 15 of the cannula 4 (see FIG. 3*d*) and is applied only along a part of the length of the mandrel 7. The layers 11 and 12 overlap and blend into each other to form a smooth transition area 14 between the first and second axial sections 13, 15 that extends over a length of at least 10 μm.

Figure 3D:
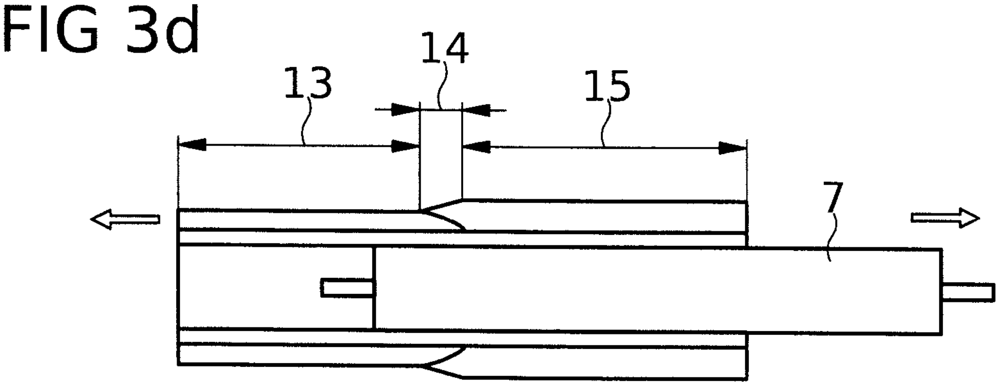
Figure 4A:
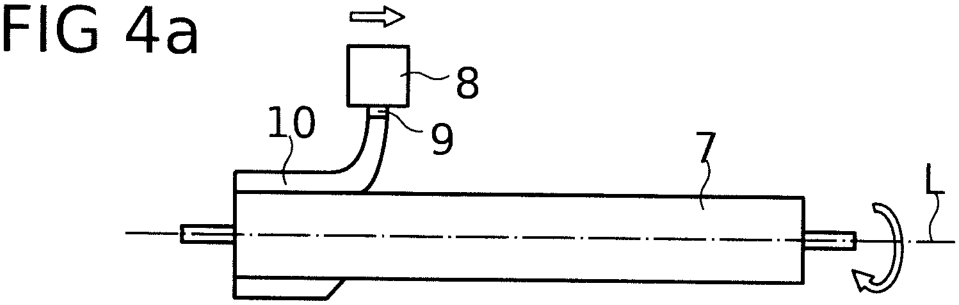
FIGS. 4*a* to 4*d* show steps of a method of manufacturing the cannula according to another embodiment.
Figure 4B:
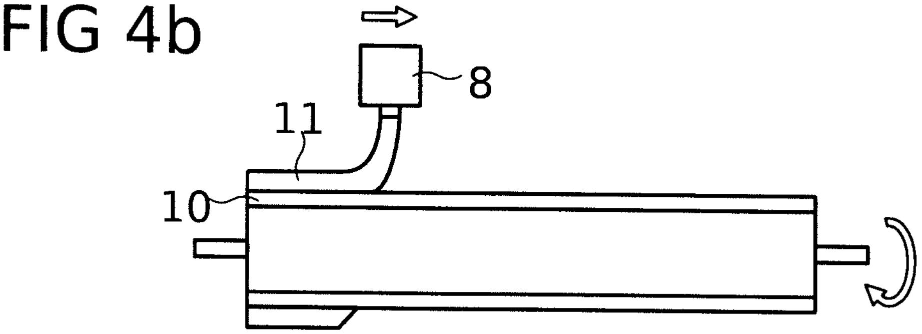
Figure 4C:
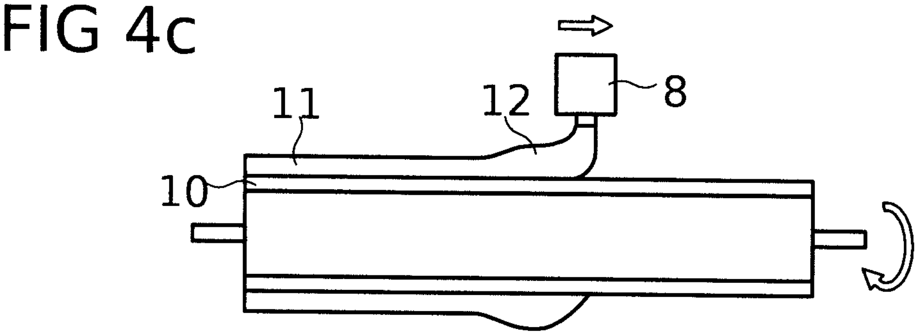
Figure 4D:
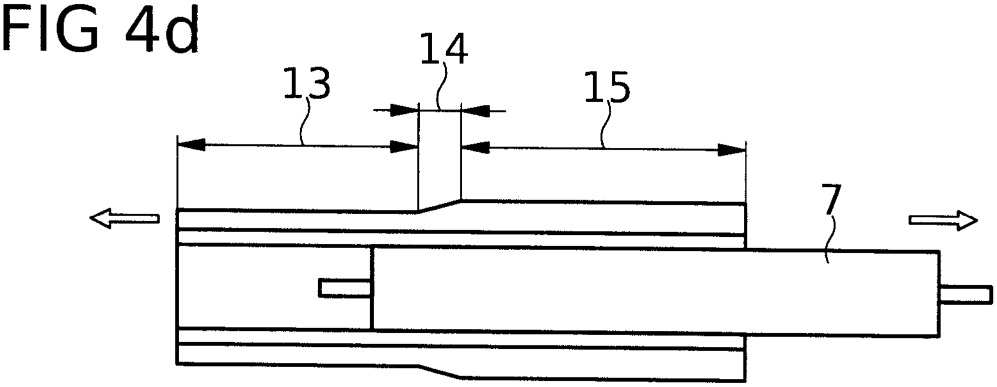
Figure 5A:
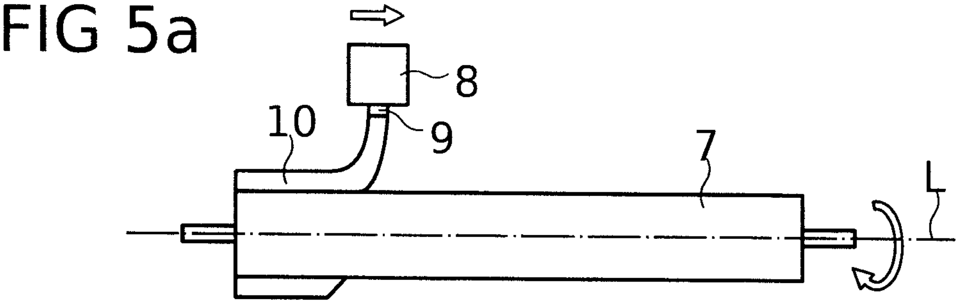
FIGS. 5*a* to 5*d* show steps of a method of manufacturing the cannula according to still another embodiment.
Figure 5B:
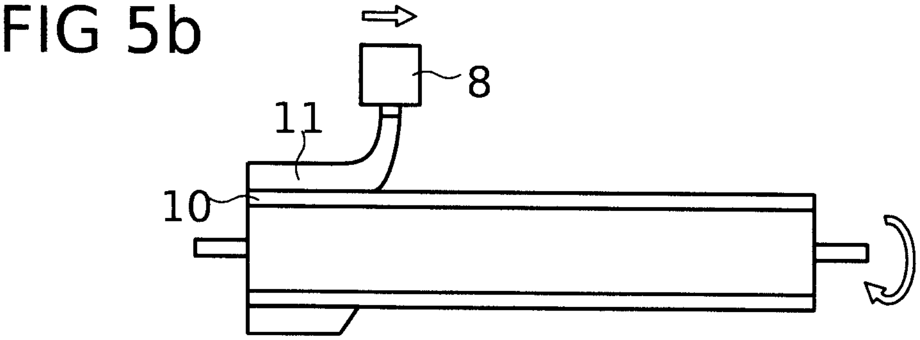
Figure 5C:
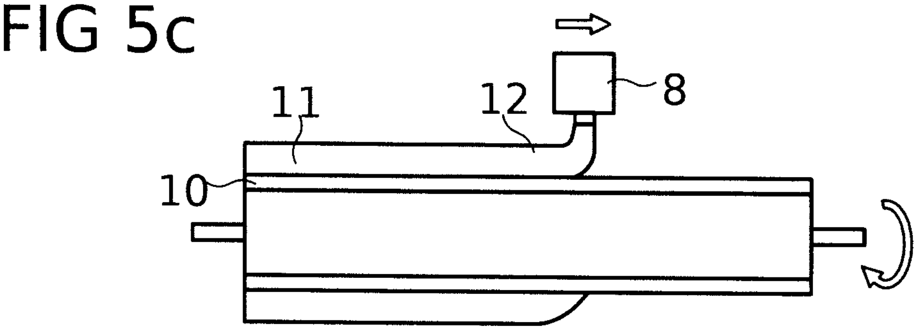
Figure 5D:
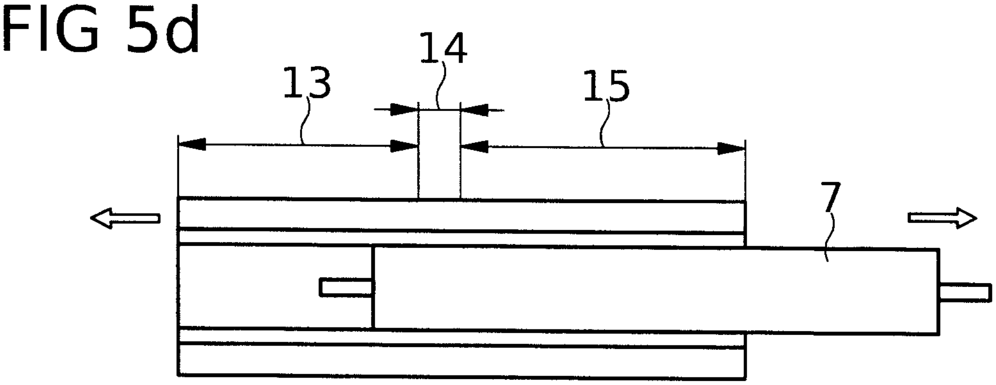

By appropriately choosing materials and wall thicknesses of the layers 11 and 12, the bending stiffnesses of the first and second axial sections 13 and 15 can be adjusted as desired. It will be appreciated that the first and second axial sections 13, 15 each preferably comprise more than one layer of material. In other words, more than one layer 11 and more than one layer 12 are applied onto the mandrel 7 to form the first axial section 13 and the second axial section 15, respectively. Apart from that, more than two axial sections connected by respective transition areas can be created on the mandrel 7. For example, sections of low bending stiffness may be created so as to alternate with sections of high bending stiffness in order to create a cannula having stiff portions connected by flexing portions. After the desired amount of material has been applied onto the mandrel 7 and sufficiently cured, the mandrel 7 is removed from the cannula 4 as indicated in FIG. 3*d.*

FIGS. 4*a* to 4*d* show substantially the same method as FIGS. 3*a* to 3*d*. The only difference is that the material of the layer 12 is the same material as the material of the layer 11. The different bending stiffnesses of the first axial section 13 and the second axial section 15 result from different wall thicknesses. FIGS. 5*a* to 5*d* show substantially the same method as FIGS. 3*a* to 3*d*. In this embodiment, the materials of the layers 11 and 12 are different but the wall thickness is constant along the length of the cannula 4, i.e. the wall thicknesses of the first axial section 13 and the second axial section 15 are the same. The different bending stiffnesses result from the different materials. As shown particularly in FIG. 5*d*, the different materials of the first and second axial sections 13, 15 blend into each other in the transition area 14. Alternatively, also referring to FIGS. 5*a* to 5*d*, the materials of the layers 11 and 12 may be the same but may comprise a different proportion of solvent and blend into each other in the transition area. For instance, the layer 11 may comprise less solvent than the layer 12, which would result in different wall thicknesses of the layers 11 and 12 (i.e. the first and second axial sections, 13, 15) after curing (not shown).

Figure 6:
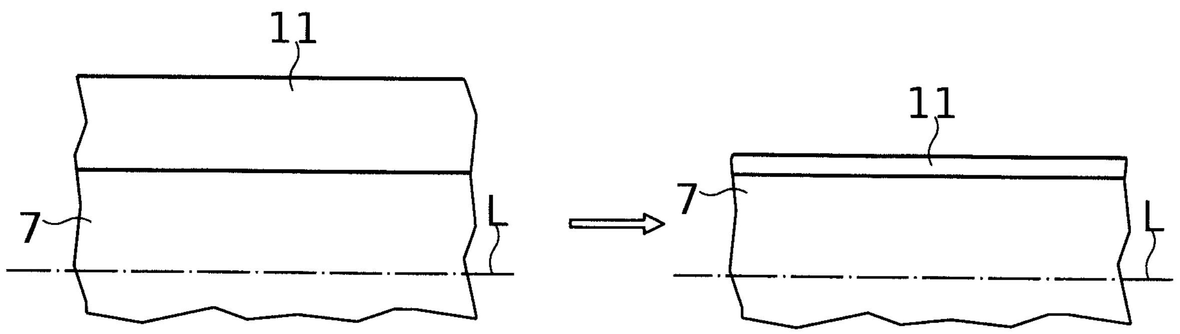
FIG. 6 shows a layer of the cannula before and after evaporation of a solvent.

Referring now to FIG. 6, and as already mentioned briefly above, the liquid materials preferably comprise a solvent. The proportion of the solvent in each material may be more than 80 vol %, preferably more than 90 vol %. The principle is exemplarily shown with respect to the layer 11 in FIG. 6. FIG. 6 shows the layer 11 applied on the mandrel 7 before evaporation of the solvent (left) and after evaporation of the solvent (right). After evaporation of the solvent, which can be denoted as "physically drying", the thickness of the applied is reduced approximately by the amount of the solvent. Using a high proportion of a solvent facilitates manufacture of very thin layers as most of the applied material will evaporate. In other words, a relatively large amount of material can be dispensed, while only a small amount of material will be present in the completed cannula 4. This is easier than applying a small amount without a solvent to create a thin layer and requires less accuracy for the dispenser.

FIGS. 7 to 11 show different aspects that may be included in a cannula 4 either alone or in any combination. For the sake of simplicity, the cannula 4 is shown as an integral piece in FIGS. 7 to 11. However, the cannula 4 comprises different layers and axial sections as described above.

Figure 7:
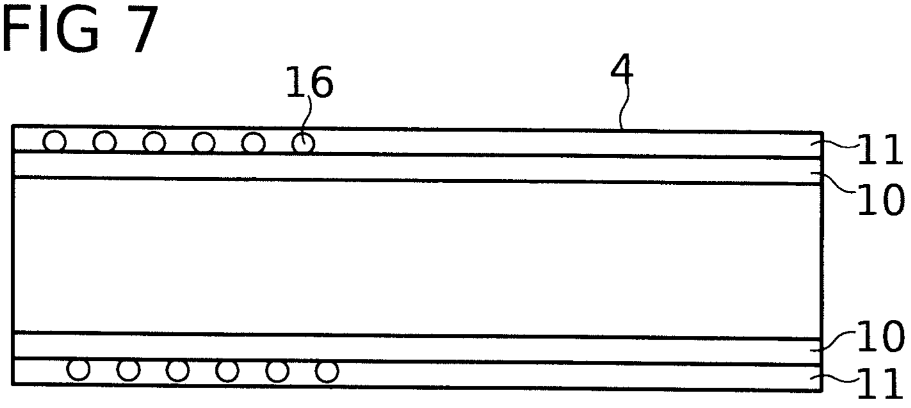
FIG. 7 shows a cannula with a stiffening structure.

The cannula 4 shown in FIG. 7 comprises a stiffening structure 16 embedded in a wall of the cannula 4. The stiffening structure 16 may have a helical shape extending about the cannula 4 or may form any other suitable pattern that strengthens the cannula 4. The stiffening structure 16 may be created by dispensing a liquid material by means of the dispenser 8. However, rather than creating a continuous layer as described above, the liquid material for the stiffening structure 16 is applied along a helical path on the mandrel 7. This material is applied onto previously created layers and covered by subsequent layers such that the stiffening structure 16 is embedded in the wall of the cannula 4. For instance, the stiffening structure 16 may be made of polyurethane, while the surrounding material is polyethylene, which is softer than polyurethane. In particular, the stiffening structure 16 has a higher elastic modulus than the rest of the wall of the cannula 4.

Alternatively or in addition, the cannula may comprise a stiffening structure formed of a helical Nitinol wire, which is pre-wound and incorporated in the cannula 4 during the dispensing process to be embedded in the wall of the cannula 4. Further alternatively, a polymer thread may be wound about the mandrel between material layers of the cannula. As mentioned above, any above-described stiffening structure is advantageously embedded between layers of the cannula 4. For instance, a first layer of material may be applied followed by the stiffening structure (e.g. liquid material along a path, pre-wound Nitinol wire or polymer thread), which is subsequently covered by one or more further layers of material. This is exemplarily indicated by layers 10 and 11 in FIG. 7. It will be appreciated that the cannula 4 may comprise more layers than the layers 10 and 11 in FIG. 7.

Figure 8:
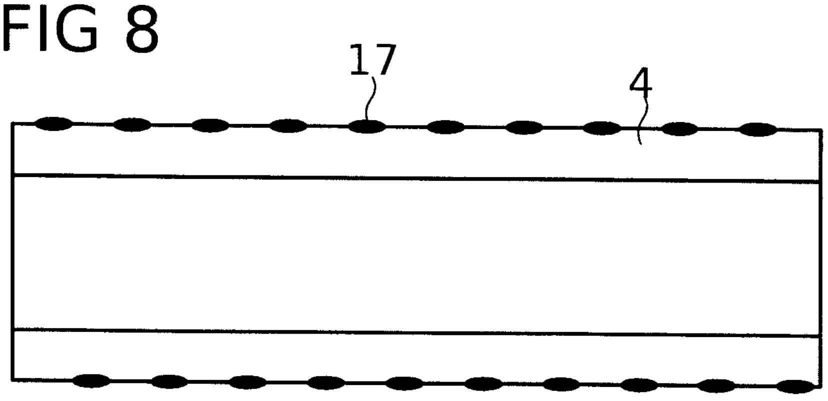
FIG. 8 shows a cannula with a marking.

Referring now to FIG. 8, a cannula 4 is shown having a marking 17 that is visible by the human eye, e.g. by exhibiting a different color than the surrounding material, or that is visible under x-ray, i.e. radiopaque. The marking 17 may be applied on the cannula 4 or embedded in the cannula 4. The marking may extend along a helical path or along any other desired path. It can be manufactured by dispensing a liquid material as described above with respect to the stiffening structure 16. Also, the wire or thread as described above may carry the marking. For instance, the wire or thread may be radiopaque.

Figure 9:
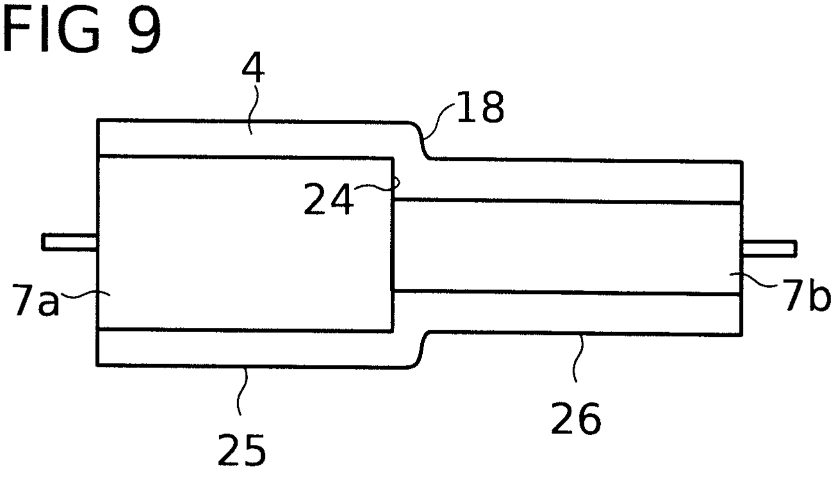
FIG. 9 shows a cannula on a mandrel having a circumferential shoulder.

FIG. 9 shows a cannula 4 having a circumferential shoulder 18, i.e. the cannula 4 has sections 25, 26 that differ in their respective inner and outer diameters. Accordingly, the mandrel 7 has a respective circumferential shoulder 24 interconnecting two mandrel parts 7*a*, 7*b* with different diameters. In order to facilitate removal of the mandrel 7 from the finished cannula 4, the parts 7*a*, 7*b* are separable.

Figure 10:
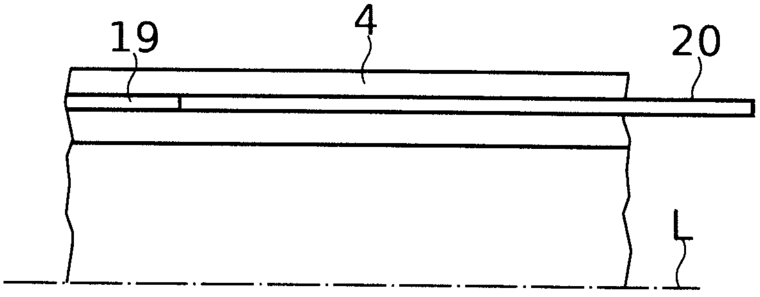
FIG. 10 shows a detail of the cannula during manufacture of a lumen in the cannula.

The cannula 4 shown in FIG. 10 has a lumen 19 extending through the wall of the cannula 4. The lumen 19 can be created by incorporating a filament 20 during the above-described dispensing method. If the filament 20 is solid, it will be pulled out of the cannula 4 after the production of the cannula 4 is finished to form the lumen 19. Alternatively, a hollow filament may be used that is embedded in the cannula 4 to form the lumen 19.

Figure 11:
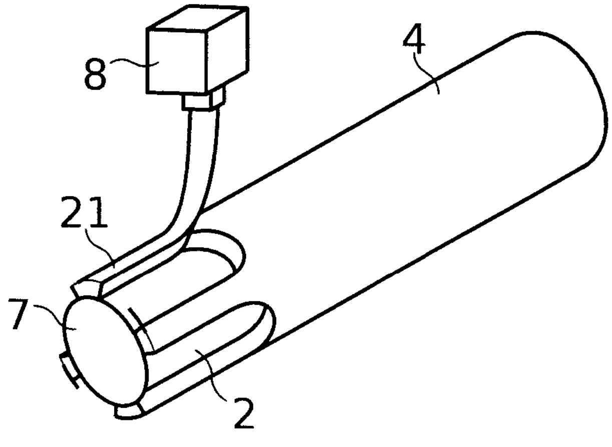
FIG. 11 shows a perspective view of a 3D printing process of an inflow cage of the cannula.

The method of manufacturing the cannula 4 may further comprise the step of creating at least one opening in the cannula 4, e.g. the aforementioned blood flow inlet 2, as shown in FIG. 11. A cage structure 21 or the like can be created by means of the dispenser 8 to form the openings 2. For this purpose, the mandrel 7 is preferably not rotated or rotated very slowly, depending on the desired shape of the cage structure 21. For instance, the mandrel 7 should not be rotated if longitudinal struts are created. The viscosity of the dispensed material of the cage structure 21 is chosen such that the material will not drop from the mandrel 7 but will blend with the previously or subsequently applied layers of the cannula 4 to form an integral body.

The method of manufacturing a cannula including the dispensing steps as described above allows manufacture of a cannula with adjustable characteristics along the length of the cannula, including any desired structure. The aforementioned features can be included alone or in combination into a cannula. The wall thickness may be influenced by a variety of parameters, such as type of material, dispensed amount of material, dispensing rate, speed of movement of one or both of the mandrel and the dispenser, and proportion of solvent in the materials etc. It will be appreciated that any desired number, order and arrangement of layers can be included in the cannula. Any number, order and arrangement of axial sections with different characteristics, such as bending stiffness, can be created as desired. The described embodiments are for illustrative purposes and not intended to be limiting. The invention is defined in the appended claims.

The invention claimed is:

1. A cannula for an intravascular blood pump comprising:
an elongate tubular body with a blood flow inlet and a blood flow outlet, the elongate tubular body comprising a first axial section comprising a first material and a second axial section comprising a second material,
wherein the first axial section and the second axial section have different bending stiffnesses,
wherein the first material and the second material blend into each other in a transition area such that no distinct borders can be determined between the first axial section and the second axial section, and
wherein the first axial section and the second axial section differ in at least one of the first material and the second material, and a first wall thickness of the first axial section and a second wall thickness of the second axial section, respectively, and, wherein the different bending stiffnesses result from at least one of a differing first material and second material, and a differing wall thickness of the first axial section and the second axial section, respectively.

2. The cannula for the intravascular blood pump of claim 1, wherein the first material and the second material are different and axially overlap in the transition area.

3. The cannula for the intravascular blood pump of claim 1, wherein the first axial section is a proximalmost section or a distalmost section of the elongate tubular body and has a greater bending stiffness than the second axial section or the rest of the elongate tubular body.

4. The cannula for the intravascular blood pump of claim 1, wherein the elongate tubular body comprises an embedded stiffening structure made of a plastic material.

5. The cannula for the intravascular blood pump of claim 1, wherein the elongate tubular body comprises an embedded stiffening structure made of a metal, a shape memory material, or may be made of a polymer.

6. The cannula for the intravascular blood pump of claim 1, wherein the elongate tubular body comprises a helical wire.

7. The cannula for the intravascular blood pump of claim 6, wherein the helical wire is embedded between a layer of the first material and a layer of the second material.

8. The cannula for the intravascular blood pump of claim 1, comprising at least one marking extending on or embedded in the elongate tubular body, wherein the at least one marking is visually perceptible or radiopaque.

9. The cannula for the intravascular blood pump of claim 1, wherein the elongate tubular body has a circumferential shoulder interconnecting two axially adjacent sections of the elongate tubular body with different diameters.

10. The cannula for the intravascular blood pump of claim 1, wherein the elongate tubular body comprises at least one lumen extending in a wall of the elongate tubular body.

11. The cannula for the intravascular blood pump of claim 1, wherein the elongate tubular body has a wall thickness in a range from about 50 μm to about 500 μm.

12. The cannula for the intravascular blood pump of claim 1, wherein the transition area extends over an axial length of at least 10 μm.

13. The cannula for the intravascular blood pump of claim 1, wherein the cannula for the intravascular blood pump is attached to a housing of a pumping device of the intravascular blood pump.

14. The cannula for the intravascular blood pump of claim 13, wherein the housing of the pumping device of the intravascular blood pump is made of a metal.

15. The cannula for the intravascular blood pump of claim 14, wherein the cannula is made of a plastic material selected from silicone, polyethylene, or polyurethane.

* * * * *